(12) United States Patent
Villette et al.

(10) Patent No.: US 9,586,006 B2
(45) Date of Patent: Mar. 7, 2017

(54) SURGICAL INSTRUMENT FOR INJECTING A PHARMACEUTICAL PRODUCT THROUGH DENSE TISSUE OF A HUMAN OR ANIMAL BODY

(75) Inventors: Olivier Villette, Andreze (FR); Vincent Guist'hau, Coron (FR)

(73) Assignee: DENTALHITEC, Mazieres en Mauges (FR)

( * ) Notice: Subject to any disclaimer, the term of this patent is extended or adjusted under 35 U.S.C. 154(b) by 439 days.

(21) Appl. No.: 12/961,532

(22) Filed: Dec. 7, 2010

(65) Prior Publication Data

US 2011/0152793 A1    Jun. 23, 2011

(30) Foreign Application Priority Data

Dec. 17, 2009  (FR) ...................................... 09 59144

(51) Int. Cl.
| | |
|---|---|
| *A61M 5/20* | (2006.01) |
| *A61M 5/24* | (2006.01) |
| *A61M 5/48* | (2006.01) |
| *A61M 5/32* | (2006.01) |

(52) U.S. Cl.
CPC ................ *A61M 5/20* (2013.01); *A61M 5/24* (2013.01); *A61M 5/482* (2013.01); *A61M 2005/2407* (2013.01); *A61M 2005/2437* (2013.01); *A61M 2005/3289* (2013.01)

(58) Field of Classification Search
CPC . A61C 1/181; A61M 5/24; A61M 2005/2407; A61M 2005/3289; A61M 5/20; A61M 5/482

USPC ........ 604/187, 188, 208–211, 218, 232, 234, 604/235; 433/80–90, 165, 166; 606/80
See application file for complete search history.

(56) References Cited

U.S. PATENT DOCUMENTS

| | | | | |
|---|---|---|---|---|
| 5,571,013 | A * | 11/1996 | Novak | 433/132 |
| 5,927,976 | A | 7/1999 | Wu | |
| 6,520,928 | B1 * | 2/2003 | Junior | 604/30 |
| 2005/0261693 | A1 * | 11/2005 | Miller et al. | 606/80 |
| 2006/0106363 | A1 | 5/2006 | Aravena et al. | |
| 2006/0189920 | A1 * | 8/2006 | Seeh | 604/22 |
| 2007/0010789 | A1 * | 1/2007 | Peter et al. | 604/155 |
| 2007/0065774 | A1 * | 3/2007 | Pernot et al. | 433/126 |

(Continued)

FOREIGN PATENT DOCUMENTS

| | | |
|---|---|---|
| EP | 2 022 522 A1 | 2/2009 |
| FR | 09 591 144 | 8/2010 |

(Continued)

*Primary Examiner* — Kami A Bosworth
(74) *Attorney, Agent, or Firm* — Leydig, Voit & Mayer, Ltd.

(57) ABSTRACT

A surgical instrument for perforating dense tissue of a human or animal body and for injecting a pharmaceutical product behind the tissue. The instrument includes a hand-piece with a housing for a pharmaceutical product container. The hand-piece has two opposite ends, one of which includes an axial throughway leading into the housing for passing a perforator injection needle inserted in the container. The other end is used to drive the container and needle in rotation. The surgical instrument further includes a member that, during perforation, can exert pressure on the pharmaceutical product in the container inserted in the housing to prevent perforation debris from entering into the needle.

9 Claims, 3 Drawing Sheets

(56) References Cited

U.S. PATENT DOCUMENTS

2007/0087308 A1* 4/2007 Flock et al. .................. 433/132
2009/0030376 A1   1/2009 Teufelberger et al.
2010/0049126 A1* 2/2010 Bronfeld et al. ............. 604/113

FOREIGN PATENT DOCUMENTS

WO    WO 98/53757 A1    12/1998
WO    WO 2009/098666 A1  8/2009

* cited by examiner

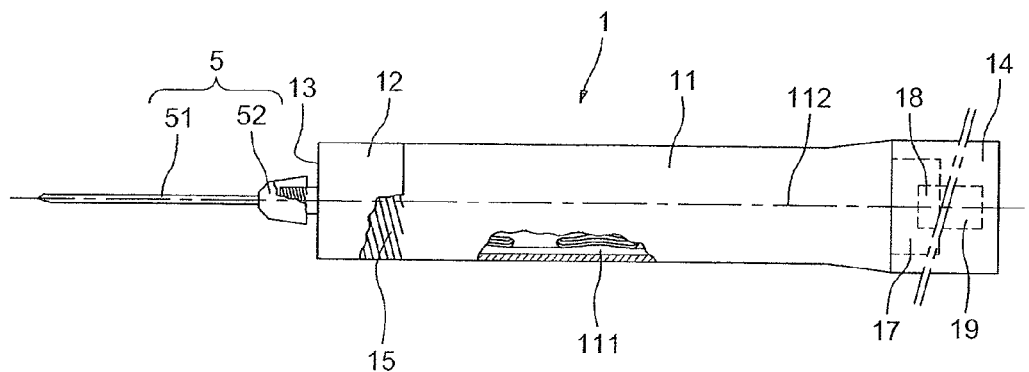
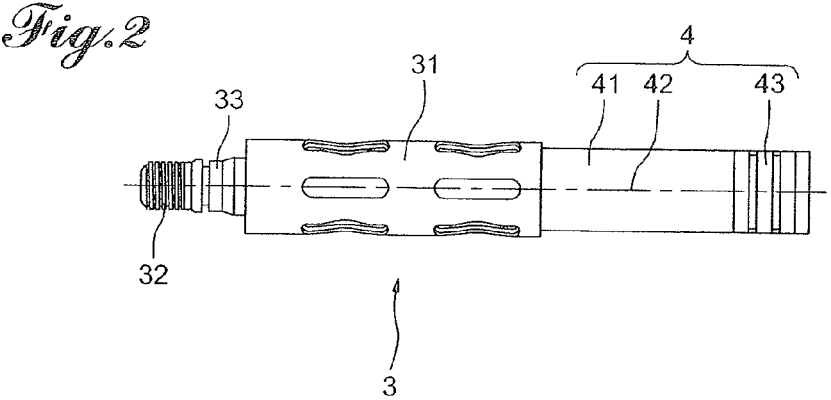
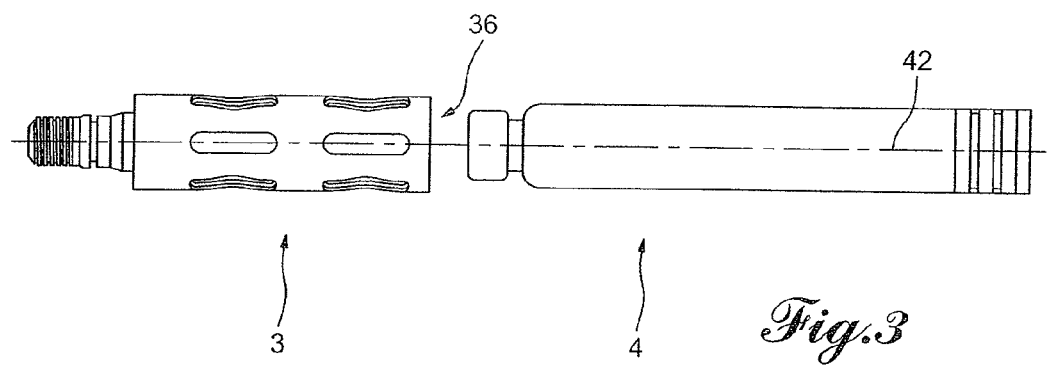

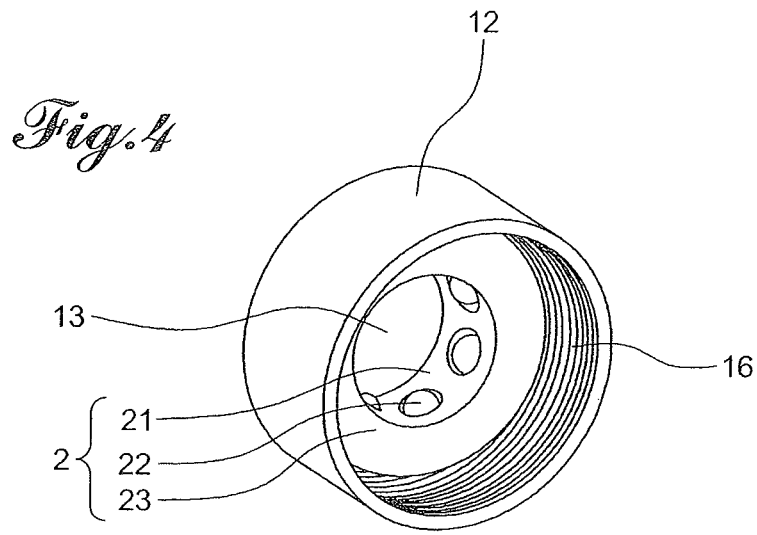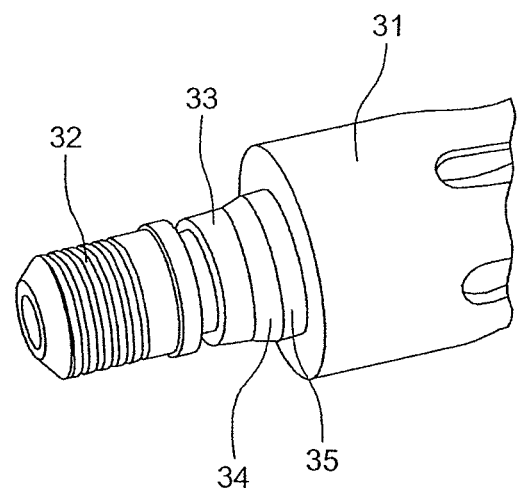

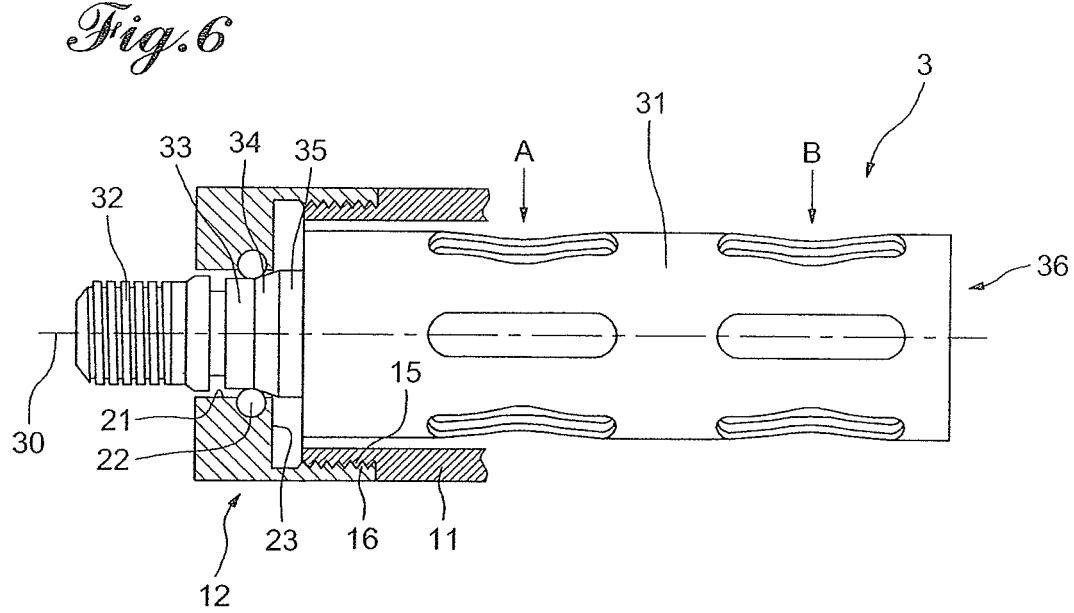

SURGICAL INSTRUMENT FOR INJECTING A PHARMACEUTICAL PRODUCT THROUGH DENSE TISSUE OF A HUMAN OR ANIMAL BODY

FIELD OF THE INVENTION

The present invention concerns a surgical instrument for perforating dense tissue of a human or animal body, and for subsequently injecting a pharmaceutical product into a body region accessible through the dense tissue, and a method for perforation and injection using said instrument.

BACKGROUND

In some medical applications, for example in the field of dental anaesthesia, it is necessary to pass through dense tissue, e.g., the cortical bone of a jawbone so that it is possible to inject a pharmaceutical product at the proper site. To arrive thereat, first a drill is used for perforation followed by injection using a needle. In this case, the perforation hole must be located with the injection needle. Additionally, since the injection needle is of smaller diameter, there is risk of leakage of the pharmaceutical product via the perforation hole during injection. Also, this two-step application requires the use of two different instruments, namely a perforator and a syringe, which increases operating time.

According to an alternative method, a perforator needle is used for perforation and for injection. This saves time and avoids leakage of pharmaceutical products, since the perforation hole is of the same diameter as the needle. However, this alternative method gives rise to the problem of obstruction of the needle lumen on account of debris generated during perforation. One solution consists of injecting a liquid between each entry phase of the needle to clear the lumen of any debris, but the efficacy thereof is limited.

By choosing a suitable rotation speed for the perforator needle or by using a needle with specific bevels, it is possible to arrive at reducing, but not eliminating, the level of needle obstruction.

SUMMARY OF THE INVENTION

The object of the invention is, therefore, to overcome the above-described disadvantages.

The object of the invention is achieved with a surgical instrument for perforating dense tissue of a human or animal body and for injecting a pharmaceutical product into a body region accessible through the dense tissue, the instrument comprising a hand-piece having a body with a housing to house a cylindrical holder freely rotatable about a longitudinal axis of the cylindrical holder conformed to receive a pharmaceutical product container that is exchangeable and joined in rotation with the holder.

The body of the surgical instrument has two opposite ends of which one is provided with an axial throughway leading into the housing and which is adapted to pass a perforator injection needle fixed to one of the two opposite ends of the cylindrical holder and intended to be inserted in the container, and whose other end comprises means to drive the container and needle in rotation.

The surgical instrument comprises a member adapted so that, during perforation, it is able in controlled manner to exert pressure on at least one predetermined quantity of pharmaceutical product present in the container fitted into the housing, to prevent perforation debris from entering into the lumen of the needle.

The member acting on the pharmaceutical product and more precisely on a piston integrated in the container, advantageously comprises its own control electronics so that during a perforation phase it is able to insert small quantities of pharmaceutical product into the lumen of the needle. These control electronics can be programmed for example so that the product is added to the needle in relation to the progress made by perforation, or so that the pharmaceutical product is held under pressure throughout the entire duration of perforation.

Insofar as the needle lumen is filled with a pharmaceutical product under pressure, the debris resulting from perforation cannot enter therein and therefore cannot cause an obstruction for the needle.

The instrument of the invention may have at least one of the following additional characteristics, taken alone or in any technically possible combination:

the instrument comprises a cylindrical holder conformed, in exchangeable manner, to receive a pharmaceutical product container, the cylindrical holder being adapted both so that it can be arranged in the housing of the hand-piece, freely rotatable about a longitudinal axis of the cylindrical holder, and to drive the container in rotation;

the axial throughway is provided with a coaxial mechanical bearing acting as bearing surface for one end of the cylindrical holder;

the hand-piece comprises an elongate body comprising the housing to receive the cylindrical holder and container, the body having a head provided with the axial throughway, and at the opposite end a removable bottom part comprising the means to drive the container in rotation;

the head is a separate element mounted removably on the body;

the end of the cylindrical holder facing the axial throughway is provided with a circumferential bearing raceway intended to cooperate with the mechanical bearing;

the circumferential bearing raceway is formed by an annular element, in metal or synthetic material, depending on the applied forces;

the mechanical bearing is an oblique ball bearing adapted to withstand an axial load;

the member acting on the pharmaceutical product is adapted so that, during the perforation of dense tissue of the human or animal body, it can insert predetermined quantities of pharmaceutical product into the perforator needle in relation to the progress of perforation;

the instrument comprises an electronic control module connected to the member acting on the container and having a memory to store instructions for the injection of predetermined quantities of pharmaceutical product in relation to the progress made by perforation;

the member acting on the pharmaceutical product is adapted itself to drive the container and, via the cylindrical holder, the perforator needle in rotation, or to be driven by driving means to which it is connected.

The object of the invention is also achieved with a method for perforating dense tissue of a human or animal body, and for injecting a pharmaceutical product into the human or animal body previously perforated with an instrument of the type described in the foregoing equipped with a perforator needle.

According to the invention, the method comprises a step to insert and to hold under pressure at least one predetermined quantity of pharmaceutical product in the needle during the perforating phase.

Said method may have the following additional characteristics, taken alone or in any technically possible combination:

the pharmaceutical product is added to the needle in relation to the progress of perforation;

the needle is maintained filled with pharmaceutical product throughout the duration of perforation to avoid obstruction thereof;

the perforation phase is followed by the injection of a treatment pharmaceutical product into the human or animal body.

BRIEF DESCRIPTION OF DRAWING FIGURES

Other characteristics and advantages of the present invention will become apparent from the following description of one embodiment of the instrument according to the invention and of the implementation of a method according to the invention. The description is given with reference to the drawings in which:

FIG. 1 illustrates a surgical instrument according to the invention;

FIG. 2 illustrates a cylindrical holder with a cartridge as pharmaceutical product container, in the assembled state;

FIG. 3 shows the cylindrical holder and separated cartridge;

FIG. 4 gives an inner view of the head of the surgical instrument;

FIG. 5 shows the end of the cylindrical holder intended to be housed in the head of the surgical instrument; and FIG. 6 illustrates the cylindrical holder bearing upon the mechanical bearing of the head of the surgical instrument.

DETAILED DESCRIPTION

FIG. 1 is a schematic side view, with cutaway portions, of a surgical instrument according to the invention.

The instrument comprises a hand-piece 1 having an elongate body 11 with a housing 111 and two opposite ends 12, 14. The end 12 is formed by a removable head provided with an axial throughway 13. The head 12 is advantageously conformed to be attached to the body 11 by screwing, the body 11 being provided for this purpose with a thread 15 and the head 12 with a thread 16 (see FIG. 4). However, the head 12 could just as well be fixed by press-fitting or it could be made in one piece with the body 11. The end 14 of the hand-piece 1 is formed by a bottom part mounted by press-fitting or, according to an embodiment that is not illustrated, by screwing onto a connector 17 of the body 11.

The body 11 of the hand-piece 1 is conformed so that, in the housing 111 which is symmetrical in rotation about an axis 112, it can receive a cylindrical holder 3 and a container 4 for a pharmaceutical product, the pharmaceutical product being a solution for injection. The container 4 comprises a rotating cylindrical body 41 (see FIG. 2) with an axis 42 and a piston 43 to act on the content. When in use, the container 4 is fitted into the cylindrical holder 3 as shown FIG. 2.

The cylindrical holder 3 is a hollow, elongate element with a neck provided with a threaded part 32 at one of its two opposite ends, and with an axial opening 36 to insert the container 4 at the other end. The holder 3 is formed so that the neck is housed within the axial throughway 13 of the head 12 of the hand-piece 1 and projects outwardly from the latter via the threaded part 32 of the neck so that it is able to receive a perforator needle 5 by screwing. For this purpose the needle 5, in addition to a cannula 51, comprises a threaded end piece 52 for attachment.

The bottom part 14 maintains the cylindrical holder 3 inside the elongate body 11 and holds it bearing against an inner part of the head 12 conformed for this purpose, as described below with reference to FIG. 6.

In addition, the bottom part 14 comprises a member 18 conformed to bear upon a piston 43 of the container 4 to exert pressure on the pharmaceutical product contained in the container 4. The member 18 is configured not only so that it is possible to inject a determined dose of the pharmaceutical product into the human or animal body, but also to insert the pharmaceutical product once or several times into the needle 5 and to hold it under pressure in accordance with operating criteria described below in the remainder of the description. The bottom part 14 also houses driving means 19 used to set the holder/container assembly in rotation about the longitudinal axis 42 of the body 41 of the container 4.

FIGS. 2 and 3 respectively illustrate an assembled state and a separated state of the cylindrical holder 3 and the pharmaceutical product container 4. The cylindrical holder 3 comprises a hollow, elongate body 31 made in a rigid plastic material. The tubular body 31 is closed at one of its two opposite ends by the above-mentioned threaded neck which is conformed to carry the perforator needle 5. The neck is provided with a lumen through which the needle 5 first enters inside the body 31 and then passes through the elastic seal of the container 4 into the latter. Therefore, by pressing on the piston 43, the pharmaceutical product leaves the container 4 via the needle 5 and is injected into a human or animal body. The neck is also provided with a circumferential bearing raceway 33 intended to and conformed to cooperate with a mechanical bearing 2 arranged in the head 12 of the hand-piece 1, as described below.

To avoid obstruction of the needle 5 by debris produced during a perforation phase, the invention proposes injecting a liquid, during the perforation phase, to lubricate and fill the needle lumen. The simplest manner is therefore to use the pharmaceutical product for this purpose. This functioning prevents debris from perforated tissue entering into the needle lumen.

However for his system to function, at least two parameters must be met:

injection must not have any influence on the rotating speed of the needle, the liquid must be injected under optimal speed and pressure.

These parameters can be met by controlling the injection parameters (e.g., speed, pressure, and encountered resistance) using an electronic syringe pump as member 18 and by placing a mechanical bearing 2, e.g., an oblique ball bearing, at the point where the holder 3/container 4 assembly bears rotatably on the head 12. In this way, the rotation speed of the needle is not reduced when the member 18 bears axially upon the piston 43, and hence on the holder 3/container 4 assembly, at the time of a rinsing injection. Therefor; the simultaneous use of pressurized liquid inside the needle (generated by an electronic syringe pump) and maintaining of optimal rotation speed by mounting a bearing on the head 12, allows needle obstruction to be eliminated as and when the needle perforates dense tissue.

FIG. 4 gives a perspective view of the inside of the head 12 of the hand-piece 1. It illustrates the inner thread 16 of the head 12 which cooperates with the outer thread 15 of the body 11 when the head 12 is fixed to the body 11, and also shows the axial throughway 13 and mechanical bearing 2 surrounding the axial throughway 13. The mechanical bearing 2 has an inner surface 21 from which the ball bearings 22 protrude, and a transverse surface 23 meeting the thread 16.

FIG. 5 shows the cylindrical holder 3 on the neck side from a perspective viewpoint with view over the faces cooperating with the mechanical bearing 2. Starting from the threaded part 32 in the direction of the body 31 of the holder 3, the neck comprises a straight cylindrical part 33 and a conical part 34 together forming a raceway for the ball bearings 22 of the mechanical bearing 2. This raceway is axially spaced away from the body 31 by a cylindrical annular surface 35 whose axial length determines the axial distance between the body 31 of the holder 3 and the transverse surface 24 of the head 12.

As can be seen FIG. 6, the above arrangements concerning the mechanical bearing 2 and the neck of the holder 3 cooperate in the following manner in the present invention.

To ensure both concentric positioning of the holder 3 in the throughway 13 of the head 12 and axial spacing between the body 31 of the holder 3 and the head 12, the mechanical bearing 2 must provide both radial support and axial support. This is achieved with an adapted arrangement of the ball bearings 22 and of the surface 21 so that when the holder 3 is housed in the hand-piece 1 with a container 4, the neck of the holder 3 and more precisely the bearing raceway formed by the straight 33 and conical 34 parts bears upon the ball bearings 22 without any other part of the holder 3 coming into contact with the head 12. The ball bearings 22 exert a force along a resultant forming a contact angle preferably of between 10° and 30° with the axis 112 of the body 11 of the hand-piece 1.

In this manner, the ball bearings cause the neck of the holder 3 to bear upon a straight concentric annular surface, here the surface 33 of the neck. At the same time, the holder 3 cannot come into contact with the transverse surface 24 of the head 12, which avoids slowing the rotation of the holder 3 at the time of pharmaceutical product injection.

According to the illustrated example of embodiment, the bearing 2 is an oblique ball bearing. However, without departing from the principle of the invention, other types of mechanical bearings can also be used, e.g., mechanical bearings containing cylindrical or conical rollers cooperating with a bevelled raceway formed on the neck instead of surfaces 33, 34. It could also be considered that, in order to cooperate with the bearing balls 22, the surfaces 33, 34 could be replaced by a curved annular surface.

The invention claimed is:

1. A surgical instrument for injecting a pharmaceutical product into a human or non-human animal body, the surgical instrument comprising:
   a cylindrical holder having opposed first and second ends, a neck at the first end of the cylindrical holder, and a longitudinal axis, wherein the cylindrical holder receives, at the second end of the cylindrical holder, a pharmaceutical product container containing the pharmaceutical product so that the pharmaceutical product container rotates with rotation of the cylindrical holder;
   a perforating needle having opposed first and second ends and rotatably attached to the neck at the first end of the cylindrical holder, wherein
      the perforating needle has, at the first end of the perforating needle, an outlet opening for ejection of the pharmaceutical product, from the pharmaceutical product container located in the cylindrical holder, in response to an axial force exerted on the pharmaceutical product along the longitudinal axis of the cylindrical holder, toward the first end of the perforating needle, and
      the second end of the perforating needle extends into the pharmaceutical product container located in the cylindrical holder; and
   a hand-piece having a hand-piece body with a housing that houses the cylindrical holder, wherein
      the hand-piece body has a longitudinal axis and the housing is symmetrical in rotation about the longitudinal axis of the hand-piece body,
      the cylindrical holder is freely rotatable about the longitudinal axis of the cylindrical holder when the cylindrical holder is housed in the housing, and
      the hand-piece body has first and second opposed ends and comprises
         a head located at the first end of the hand-piece body, the head having an axial throughway through which the neck of the cylindrical holder, with the perforating needle rotatably attached to the cylindrical holder, passes when the head is fixed to the first end of the cylindrical holder,
         a bottom part located at the second end of the hand-piece body, wherein the bottom part houses
            (i) driving means for rotating the pharmaceutical product container and, via the pharmaceutical product container, rotating the cylindrical holder and the perforating needle, and
            (ii) a member acting on the pharmaceutical product container and including an electronic control module for controlling ejection of the pharmaceutical product from the pharmaceutical product container into the perforating needle during rotation of the perforating needle and preventing perforation debris from entering the opening of the perforating needle during perforating rotation of the perforating needle, wherein the electronic module includes a memory storing instructions for injection of predetermined quantities of the pharmaceutical product in relation to progress in perforation of a human or non-human animal body by the perforating needle; and
         a coaxial ball bearing located between the head and the neck and including ball bearing balls and a raceway that has a straight cylindrical part for supporting radial forces and a conical part for supporting axial forces.

2. The surgical instrument according to claim 1, wherein the coaxial ball bearing is a mechanical ball bearing.

3. The surgical instrument according to claim 1, wherein the ball bearing balls cooperate with the raceway, and the raceway is located on the neck of the cylindrical holder.

4. The surgical instrument according to claim 1, wherein the electronic control module is an electronic syringe pump.

5. A method for perforating a human or non-human animal body and injecting a pharmaceutical product behind tissue of the human or non-human animal body with a surgical instrument according to claim 1, the method comprising: inserting and holding under pressure a predetermined quantity of the pharmaceutical product in the perforating needle during perforation of the tissue, in relation to the degree of penetration of the human or non-human body by the perforating needle, and maintaining the perforating needle full of the pharmaceutical product, under pressure, to prevent perforation debris from entering and obstructing the outlet opening of the perforating needle.

6. A surgical instrument for injecting a pharmaceutical product into a human or non-human animal body, the surgical instrument comprising:
   a cylindrical holder having opposed first and second ends and a longitudinal axis, and receiving, at the second end of the cylindrical holder, a pharmaceutical product container containing the pharmaceutical product so that the pharmaceutical product container rotates with rotation of the cylindrical holder, wherein the cylindrical holder includes, at the first end of the cylindrical holder, a projecting tubular portion having an outer surface;
   a perforating needle having opposed first and second ends and attached to the first end of the cylindrical holder, wherein
      the perforating needle has, at the first end of the perforating needle, an outlet opening for ejection of the pharmaceutical product from the pharmaceutical product container located in the cylindrical holder, in response to an axial force exerted on the pharmaceutical product along the longitudinal axis of the cylindrical holder, toward the first end of the perforating needle, and
      the second end of the perforating needle extends through the tubular portion of the cylindrical holder into the pharmaceutical product container located in the cylindrical holder; and
   a hand-piece including
      a hand-piece body having opposed first and second ends and housing the cylindrical holder so that the cylindrical holder is freely rotatable about the longitudinal axis of the cylindrical holder when the cylindrical holder is housed in the hand-piece body, wherein the hand-piece body has a longitudinal axis and the housing is symmetrical in rotation about the longitudinal axis of the hand-piece body, and the hand-piece body comprises
         a bottom part located at the second end of the hand-piece body, wherein the bottom part houses
            (i) driving means for rotating the pharmaceutical product container and, via the pharmaceutical product container, rotating the cylindrical holder and the perforating needle, and
            (ii) a member including an electronic control module for controlling ejection of the pharmaceutical product from the pharmaceutical product container into the perforating needle during rotation of the perforating needle and preventing perforation debris from entering the outlet opening of the perforating needle during perforating rotation of the perforating needle, and
         a head removably engaging the first end of the hand-piece body and including an axial throughway through which the tubular portion of the cylindrical holder and the perforating needle pass when the head is mounted on the first end of the hand-piece body, wherein
            the head includes, on an inner surface, a coaxial ball bearing including bearing balls projecting inwardly with respect to the inner surface of the head,
            the outer surface of the tubular portion of the cylindrical holder includes a straight cylindrical annular surface portion concentric with the longitudinal axis of the cylindrical holder, and a conical cylindrical surface portion oblique to and adjacent the straight cylindrical annular surface portion and concentric with the longitudinal axis of the cylindrical holder, and,
            when the head is mounted on the first end of the hand-piece body, the straight cylindrical annular surface portion and the conical cylindrical surface portion provide a raceway on which the balls bear for rotation of the cylindrical holder relative to the hand-piece body, about the longitudinal axis of the cylindrical holder, and support the axial force of ejecting the pharmaceutical product and radial forces of rotation of the perforating needle and the cylindrical holder.

7. The surgical instrument according to claim 6, wherein the straight cylindrical annular surface portion of the outer surface of the tubular portion of the cylindrical holder is farther from the second end of the cylindrical holder than is the conical cylindrical surface portion of the outer surface of the tubular portion of the cylindrical holder.

8. The surgical instrument according to claim 6, wherein the electronic control module includes a memory storing instructions for injection of a predetermined quantity of pharmaceutical products in relation to progress in perforation of the human or non-human animal body by the perforating needle.

9. A surgical instrument for injecting a pharmaceutical product into a human or non-human animal body, the surgical instrument comprising:
   a cylindrical holder having opposed first and second ends, a neck at the first end of the cylindrical holder, and a longitudinal axis, wherein the cylindrical holder receives, at the second end of the cylindrical holder, a pharmaceutical product container containing the pharmaceutical product so that the pharmaceutical product container rotates with rotation of the cylindrical holder;
   a perforating needle having opposed first and second ends and rotatably attached to the neck at the first end of the cylindrical holder, wherein
      the perforating needle has, at the first end of the perforating needle, an outlet opening for ejection of the pharmaceutical product, from the pharmaceutical product container located in the cylindrical holder, in response to an axial force exerted on the pharmaceutical product along the longitudinal axis of the cylindrical holder, toward the first end of the perforating needle, and
      the second end of the perforating needle extends into the pharmaceutical product container located in the cylindrical holder; and
   a hand-piece having a hand-piece body with a housing that houses the cylindrical holder, wherein
      the hand-piece body has a longitudinal axis and the housing is symmetrical in rotation about the longitudinal axis of the hand-piece body,
      the cylindrical holder is freely rotatable about the longitudinal axis of the cylindrical holder when the cylindrical holder is housed in the housing, and
      the hand-piece body has first and second opposed ends and comprises
         a head located at the first end of the hand-piece body, the head having an axial throughway through which the neck of the cylindrical holder, with the perforating needle rotatably attached to the cylindrical holder, passes when the head is fixed to the first end of the cylindrical holder, a bottom part located at the second end of the hand-piece body, wherein the bottom part houses a member driving the pharmaceutical product container and, via the cylindrical holder, the perforating needle in rotation and the member includes an electronic control module for controlling ejection of the pharmaceutical product from the pharmaceutical product container into the perforating needle during rotation of the perforating needle and preventing perforation debris from entering the opening of the perforating needle during perforating rotation of the perforating needle, and the electronic module includes a memory storing instructions for injection of predetermined quantities of the pharmaceutical product in relation to progress in perforation of a human or non-human animal body by the perforating needle; and a coaxial ball bearing located between the head and the neck and including ball bearing balls and a raceway that has a straight cylindrical part for supporting radial forces and a conical part for supporting axial forces.

* * * * *